United States Patent [19]

Schneider et al.

[11] 4,117,009
[45] Sep. 26, 1978

[54] METHOD OF MAKING N-[4-CHLOROPHENYL)AMINO]CARBONYL)-2,6-DIFLUOROBENZAMIDE

[75] Inventors: Louis Schneider, Elizabeth; David E. Graham, Westfield, both of N.J.

[73] Assignee: GAF Corporation, New York, N.Y.

[21] Appl. No.: 805,129

[22] Filed: Jun. 9, 1977

[51] Int. Cl.² .......................................... C07C 127/22
[52] U.S. Cl. ................................................ 260/553 E
[58] Field of Search ........................ 260/553 E, 558 R

[56] References Cited

U.S. PATENT DOCUMENTS

| | | | |
|---|---|---|---|
| 1,633,392 | 6/1927 | Boedecker ........................ | 260/553 E |
| 3,627,778 | 12/1971 | Nusslein et al. .............. | 260/553 E X |
| 4,005,223 | 1/1977 | Sirrenberg et al. .......... | 260/553 E X |
| 4,013,717 | 3/1977 | Wellings et al. ................ | 260/553 E |
| 4,068,002 | 1/1978 | Sirrenberg et al. .......... | 260/553 E X |

OTHER PUBLICATIONS

Turner, J.A.C.S. 68, pp. 1607–1608 (1946).
Nickon et al., J.A.C.S. 74, 5566 (1952) - Abstract.

*Primary Examiner*—Winston A. Douglas
*Assistant Examiner*—Thomas A. Waltz
*Attorney, Agent, or Firm*—Walter C. Kehm; W. Katz

[57] ABSTRACT

In accordance with the sought-after features of an improved process for the preparation of Dimilin, there is provided herein a process which comprises first extracting 2,6-difluorobenzamide from an aqueous acid solution with a selective solvent which is acid-stable and water-insoluble. The extract then is condensed in situ with p-chlorophenyl isocyanate at an elevated temperature to form the desired product. The selective solvent preferably has a boiling point at the reaction temperature, preferably about 120°–170° C. Finally, the product is crystallized from the selective solvent.

4 Claims, No Drawings

METHOD OF MAKING N-[4-CHLOROPHENYL)AMINO]CARBONYL)-2,6-DIFLUOROBENZAMIDE

BACKGROUND OF THE INVENTION

1. Field of the Invention

This invention relates to an improved method of making N-{[(4-chlorophenyl) amino] carbonyl}-2,6-difluorobenzamide ("Dimilin").

Dimilin, a trademark of Thompson-Hayward Chemical Company, is an important insect growth regulator, particularly for gypsy moth control. The final synthetic steps used to prepare this compound comprises treating 2,6-difluorobenzonitrile with concentrated sulfuric acid to convert it to the benzamide, and subsequently condensing with p-chlorophenyl isocyanate to form the desired product.

Since these reactions are run in a solvent, it is desired to provide an improved process in which the same solvent may serve as the extraction solvent for the benzamide, as the in situ reaction solvent for the condensation reaction, and as the crystallization solvent for the product.

Such a selective solvent thus should be capable of extracting the relatively insoluble benzamide from the aqueous, acid solution. It should have a high boiling point so that the condensation reaction may be run at elevated temperatures. Finally, it should dissolve the product selectively to enable crystallization to take place easily. These and other attributes and features of a selective solvent in accordance with the invention will be made apparent from the following, more particular, description of the invention.

SUMMARY OF THE INVENTION

In accordance with the sought-after features of an improved process for the preparation of Dimilin, there is provided herein a process which comprises first extracting 2,6-difluorobenzamide from an aqueous acid solution with a selective solvent which is acid-stable and water-insoluble. The extract then is condensed in situ with p-chlorophenyl isocyanate at an elevated temperature to form the desired product. The selective solvent preferably has a boiling point at the reaction temperature, preferably about 120°-170° C. Finally, the product is crystallized from the selective solvent.

DETAILED DESCRIPTION OF THE INVENTION

DESCRIPTION OF THE PREFERRED EMBODIMENTS

In suitable embodiments of the invention, the selective solvent is chosen from among halogenated hydrocarbons having a boiling point of at least 120° C., and preferably from among polyhalogenated hydrocarbons having from 2-10 carbon atoms, which boil at about 140°-150° C.

The selective solvent of the invention may be a straight chain or branched halogenated hydrocarbon, which satisfy the criteria stated above, and which, preferably is commercially available at a reasonable cost. Accordingly, tetrachloroethanes may be considered the solvent of choice herein, and optimally, the symmetrical 1,1,2,2-tetrachloroethane. However, other chloro or bromo hydrocarbons may be used as well.

The invention now will be illustrated more particularly with reference to the accompanying examples.

EXAMPLE

PREPARATION OF DIMILIN

A. Preparation of 2,6-Difluorobenzamide

Charged into a 500 cc 4-neck flask equipped with an agitator, thermometer, condenser and mantle were the following:

| | |
|---|---|
| 150 cc | 95% sulfuric acid |
| 15 cc | water |
| 120.5 g. | 2,6-difluorobenzonitrile (98.2% purity = 0.85 mole) |

The mixture was allowed to exotherm and then heated to 85° C for 1½ hrs. The reaction solution was cooled to 30° C and drowned into a 2 l flask with a bottom outlet containing 600 g. of ice at 0°-10° C for ½ hour.

B. Extraction of 2,6-Difluorobenzamide 450 cc of 1,1,2,2-tetrachloroethane (TCE) was added and the mixture heated to 80° C. The lower TCE layer was separated and the upper acid layer was extracted with 6 × 150 cc of TCE at 80° C. The combined TCE layer was filtered through a sodium carbonate bed which neutralized the residual sulfuric acid. Then 900 cc of TCE was distilled at 80°-90° C pot (61°-77° vapor)/150 mm.

C. Reaction with P-Chlorophenyl Isocyanate 132.5 g. of p-chlorophenyl isocyanate (0.86 mole) was then added to the TCE-benzamide intermediate and the mixture was heated at 150° C for 4 hours under a nitrogen blanket.

D. Crystallization of Product

The reaction product mixture was cooled to 10° C and suction filtered. The product cake then was washed with 150 cc of heptane, and kept separate from the TCE filtrate. The product was dried in a vacuum oven at 100° C to yield 220.5 g. (81.3% yield) (HPLC purity 97.3%) m.p. 224°-226° C.

We claim:

1. A process for the preparation of N-{[(4-chlorophenyl) amino] carbonyl}-2,6-difluorobenzamide from 2,6-difluorobenzamide which is formed by treating the corresponding nitrile with concentrated sulfuric acid solution, which comprises:

(a) extracting said 2,6-difluorobenzamide from said solution with a solvent which is water-insoluble and acid-stable, which has a boiling point of at least 120° C., wherein said solvent is a straight chain or branched polyhalogenated hydrocarbon having 2-10 carbon atoms, and from which said final product may be crystallized, (b) condensing said extract with p-chlorophenyl isocyanate at a temperature of at least 120° C. to form said desired product, and, (c) crystallizing said product from the solvent.

2. A process according to claim 1 wherein said solvent has a boiling point between about 140°-150° C.

3. A process according to claim 1 wherein said solvent is a tetrachloroethane.

4. A process according to claim 1 wherein said solvent is 1,1,2,2-tetrachloroethane.

UNITED STATES PATENT AND TRADEMARK OFFICE
CERTIFICATE OF CORRECTION

PATENT NO. : 4,117,009
DATED : September 26, 1978
INVENTOR(S) : Louis Schneider; David E. Graham It is certified that error appears in the above-identified patent and that said Letters Patent are hereby corrected as shown below:

In line 2 "Dimilin" read -- N-[(4-chlorophenyl)amino]carbonyl-2,6-difluorobenzamide --.

In Column 1, line 11, delete "("Dimilin")".

On lines 12-15, for "Dimilin, a trademark of Thompson-Hayward Chemical Company," read -- The compound --.

On line 40, for "Dimilin", read -- the compound --.

In Column 2, line 7, delete "PREPARATION OF DIMILIN".

Signed and Sealed this

Nineteenth Day of June 1979

[SEAL]

Attest:

RUTH C. MASON
Attesting Officer

DONALD W. BANNER
Commissioner of Patents and Trademarks